United States Patent [19]
Wang-Lee

[11] Patent Number: 5,970,514
[45] Date of Patent: Oct. 26, 1999

[54] FACE MASK

[76] Inventor: Min-Young Wang-Lee, No. 473, Chung-Shan S. Rd., Yung-Kang City, Tainan Hsien, Taiwan

[21] Appl. No.: 09/245,543

[22] Filed: Feb. 5, 1999

[51] Int. Cl.$^6$ .............................. A41D 13/00; A61F 9/06
[52] U.S. Cl. .............................................. 2/9; 2/10; 2/424
[58] Field of Search .............................. 2/9, 10, 15, 424, 2/441, 443, 8, 12; 52/93.1; 160/395; 312/114; 206/557; 217/10

[56] References Cited

U.S. PATENT DOCUMENTS

| | | | |
|---|---|---|---|
| 2,610,323 | 9/1952 | Johnson | 2/9 |
| 2,729,820 | 1/1956 | Anderson | 2/8 |
| 3,214,767 | 11/1965 | Weber | 2/9 |
| 3,868,727 | 3/1975 | Paschall | 2/8 |
| 4,495,657 | 1/1985 | Bay | 2/10 |
| 5,365,615 | 11/1994 | Piszkin | 2/424 |
| 5,673,431 | 10/1997 | Batty | 2/9 |
| 5,699,556 | 12/1997 | Chen | 2/9 |
| 5,765,223 | 6/1998 | McCausland | 2/9 |

FOREIGN PATENT DOCUMENTS 1098537  3/1955  France .
 49498  10/1940  Netherlands .

*Primary Examiner*—John J. Calvert
*Assistant Examiner*—Tejosh Patel
*Attorney, Agent, or Firm*—Ladas & Parry

[57] ABSTRACT

A face mask includes an arcuate transparent sheet which extends about a central axis, and which has an upper engaging edge portion extending therealong. The upper engaging edge portion has a central positioning hole formed in a middle thereof to define a reference line with the central axis, two elongated first grooves formed respectively at two side ends of the upper engaging edge portion to define a first chord therebetween perpendicular to the reference line, and two elongated second grooves respectively inboard to the first grooves. The second grooves define a second chord therebetween perpendicular to the reference line. Each of the first and second grooves extends along the upper engaging edge portion. Each second groove is longer than each first groove. As such, the face mask can be assembled on different kinds of helmets and the like.

2 Claims, 4 Drawing Sheets

FACE MASK

BACKGROUND OF THE INVENTION

1. Field of the Invention

This invention relates to a face mask, more particularly to a face mask with elongated grooves for facilitating assembly of the face mask on a helmet or the like.

2. Description of the Related Art

A conventional transparent face mask is assembled on a front brim of a helmet or a helmet frame. For example, a helmet has two pivot members to engage an upper engaging edge portion of a face mask such that the face mask can be rotated upwardly about the pivot members. Another exemplary helmet has a plurality of fastening members disposed along a front brim thereof to secure firmly a face mask for safety purpose. For different helmets and helmet frames, face masks with different engaging holes have to be manufactured. The requirement to provide face masks with different holes causes inconveniences in manufacture and inventory management.

SUMMARY OF THE INVENTION

The object of the present invention is to provide a face mask which can be assembled to a variety of helmets and helmet frames.

According to this invention, the face mask includes an arcuate transparent sheet which extends about a central axis. The transparent sheet has an upper engaging edge portion which extends therealong. The upper engaging edge portion has a central positioning hole which is formed in a middle thereof and which defines a reference line with the central axis, two elongated first grooves which are formed respectively at two side ends of the upper engaging edge portion and which define a first chord therebetween perpendicular to the reference line, and two elongated second grooves respectively inboard to the first grooves. The second grooves define a second chord therebetween perpendicular to the reference line. Each of the first and second grooves extends along the upper engaging edge portion. Each second groove is longer than each first groove. As such, the face mask can be assembled on different kinds of helmets and the like.

BRIEF DESCRIPTION OF THE DRAWINGS

Other features and advantages of the present invention will become apparent in the following detailed description of the preferred embodiment of the invention, with reference to the accompanying drawings, in which.

DETAILED DESCRIPTION OF THE PREFERRED EMBODIMENT

Figure 1:
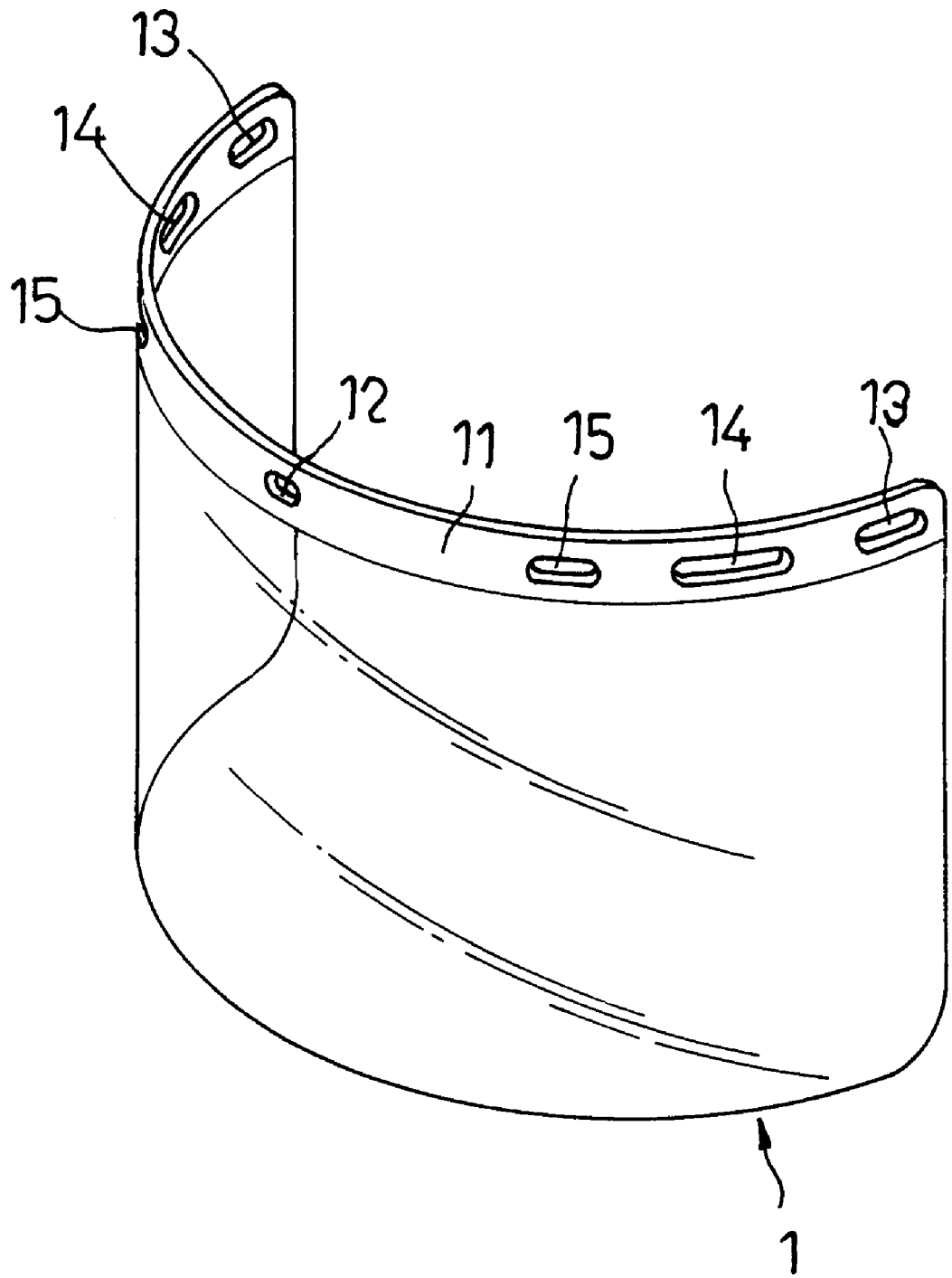
FIG. 1 is a perspective view of a preferred embodiment of a face mask according to this invention.

Referring to FIG. 1, the preferred embodiment of the face mask according to the present invention is shown to comprise an arcuate transparent sheet 1 which is made of a transparent plastic material and which extends about a central axis. The transparent sheet 1 has an upper engaging edge portion 11 which extends therealong at an upper edge thereof. The upper engaging edge portion 11 has a generally elliptical central positioning hole 12 which is formed in a middle thereof and which defines a reference line with the central axis, and two side portions which are symmetric with each other relative to the reference line. Each side portion has an elongated first groove 13, an elongated second groove 14 between the central positioning hole 12 and the first groove 13, and an elongated third groove 15 between the central positioning hole 12 and the second groove 14. Each of those grooves 13,14,15 extends along the upper engaging edge portion 11. The first grooves 13 define a first chord therebetween that is perpendicular to the reference line. The second grooves 14 define a second chord therebetween that is perpendicular to the reference line. The third grooves 15 define a third chord therebetween that is perpendicular to the reference line. The second grooves 14 are longer than the first grooves 13.

Figure 2:
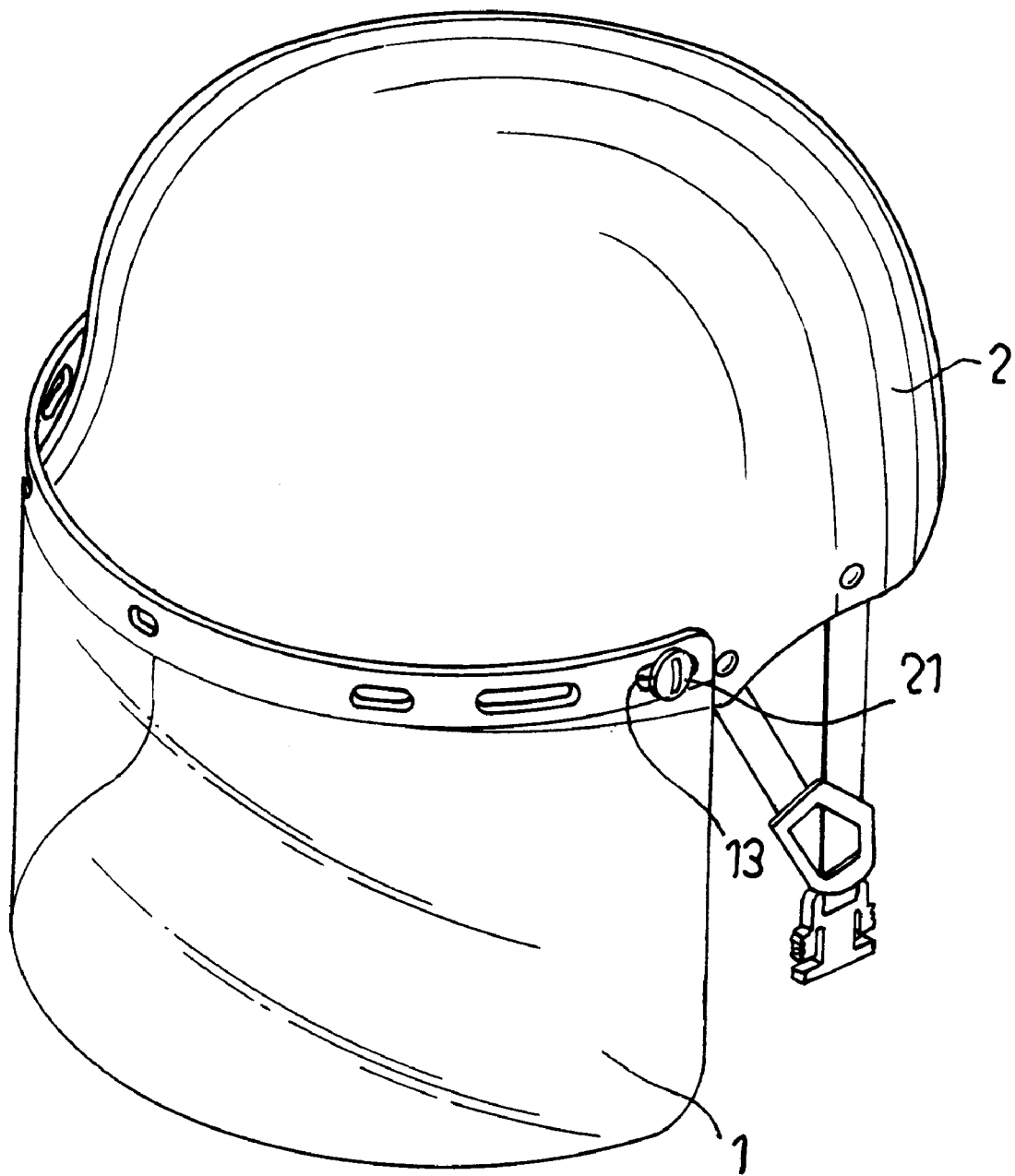
FIG. 2 is a perspective view showing the face mask assembled to a first helmet.

Referring to FIGS. 1 and 2, when assembling the face mask of this invention to a first helmet 2 which has two pivot members 21 disposed at two sides of a front brim thereof, the pivot members 21 can engage the first grooves 13, respectively, such that the face mask 1 can be rotated upwardly relative to the pivot members 21.

Figure 3:
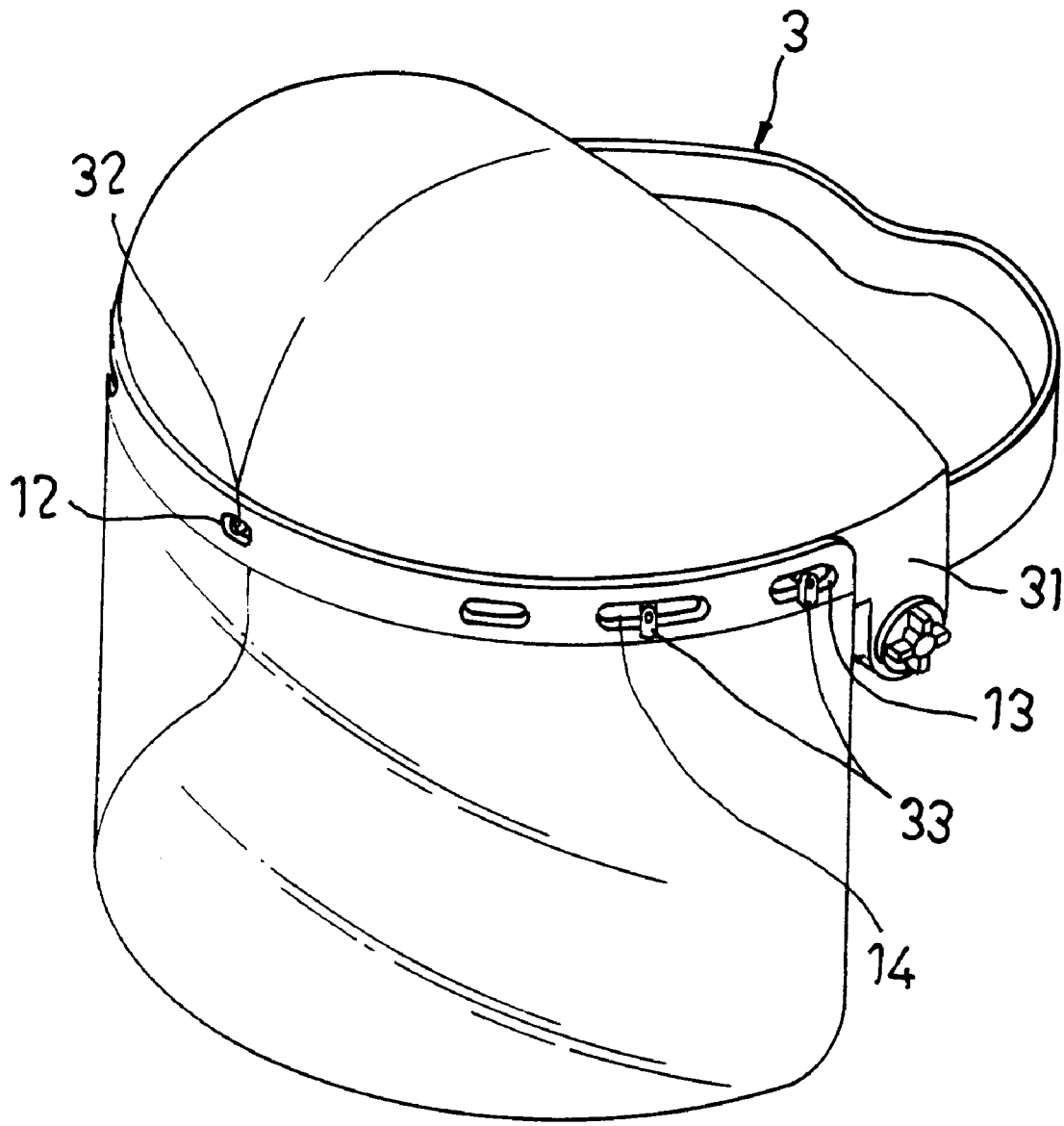
FIG. 3 is a perspective view showing the face mask assembled to a second helmet.

Referring to FIGS. 1 and 3, when assembling the face mask of this invention to a second helmet 3 which has a central positioning stud 32 disposed at a middle of a front brim 31 thereof, and four fastening members 33 disposed rotatably at two sides of the front brim 31, the central positioning hole 12 is sleeved on the central positioning stud 32 to position the face mask on the helmet 3. The fastening members 33 pass through the first and second grooves 13,14 respectively, and are then rotated so as to secure the face mask on the helmet 3 for safety purposes.

Figure 4:
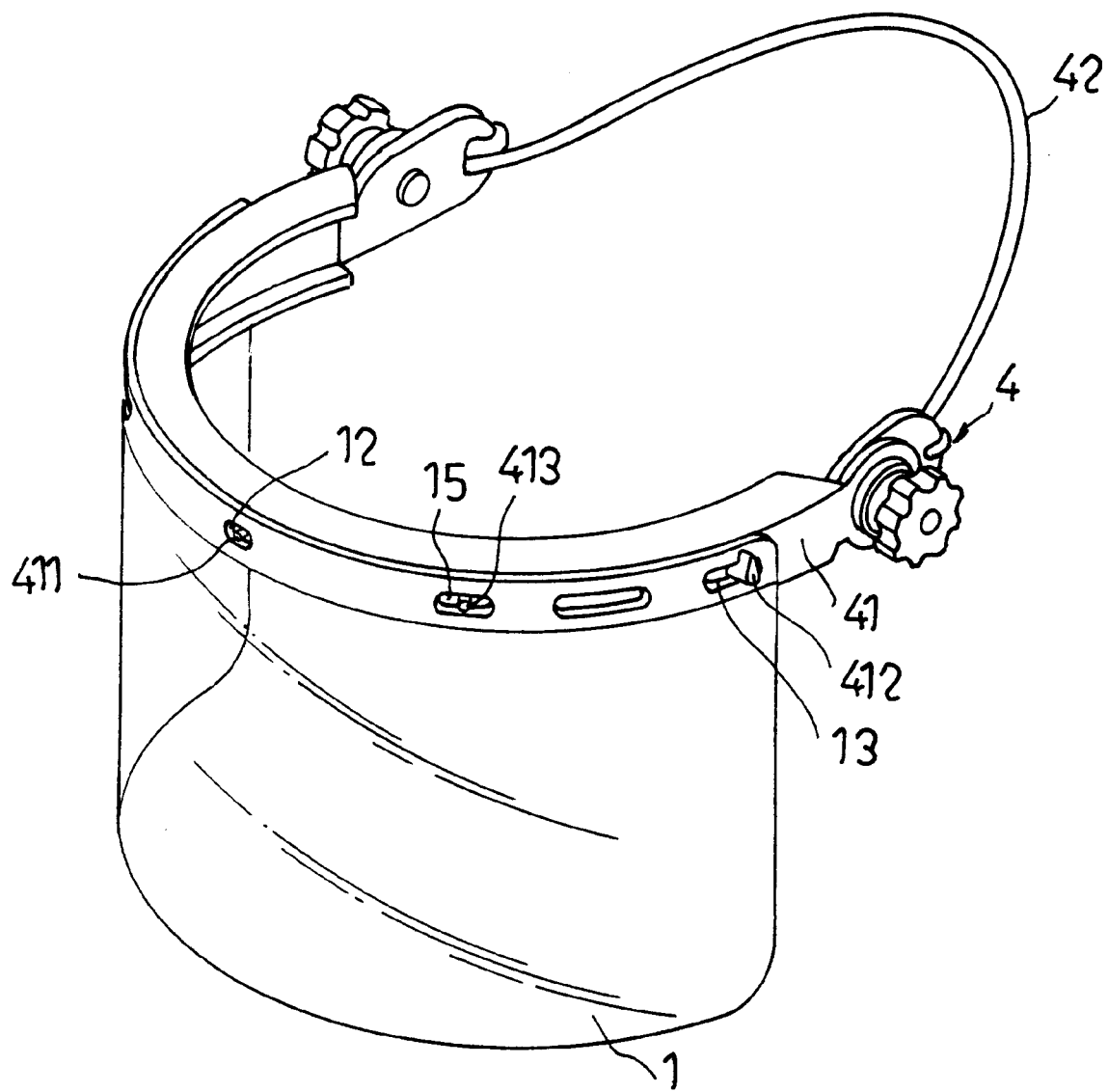
FIG. 4 is a perspective view showing the face mask assembled to a helmet frame.

The face mask of this invention can also be assembled to a helmet frame 4, as shown in FIG. 4. The helmet frame 4 is shown to have an arcuate frame 41 and a connecting cord 42 which are connected to two ends of the arcuate frame 41. The arcuate frame 41 has an arcuate front brim with a central positioning stud 411 disposed at a middle thereof, two fastening plates 412 rotatably provided on two side ends thereof, and two fastening protrusions 413 disposed between the fastening plates 412 and the positioning stud 411. Thus, the face mask is positioned on the arcuate frame 41 in such a manner that the positioning stud 411 engages the central positioning hole 12 so that the fastening plates 412 and the fastening protrusions 413 are registered with the first and third grooves 13,15, respectively. As such, the face mask can be secured on the arcuate frame 41 once the fastening plates 412 and the fastening protrusions 413 engage securely the first and third grooves 13,15, respectively.

As mentioned above, the face mask of this invention can be assembled on different kinds of helmets and helmet frames by virtue of the elongated grooves 13,14,15.

While the present invention has been described in connection with what is considered the most practical and preferred embodiment, it is understood that this invention is not limited to the disclosed embodiment but is intended to cover various arrangements included within the spirit and scope of the broadest interpretations and equivalent arrangements.

I claim:

1. A face mask, comprising:

an arcuate transparent sheet extending about a central axis, and having an upper engaging edge portion which extends along said transparent sheet and which has a central positioning hole that is formed in a middle of said upper engaging edge portion and that defines a reference line with said central axis, two elongated first grooves that are formed respectively at two side ends of said upper engaging edge portion and that define a first chord therebetween perpendicular to said reference line, and two elongated second grooves respectively inboard to said first grooves, and that define a second chord therebetween perpendicular to said reference line, each of said first and second grooves extending along said upper engaging edge portion, each of said second grooves being longer than each of said first grooves.

2. The face mask as claimed in claim 1, wherein said upper engaging edge portion further has two elongated third grooves which are respectively inboard to said second grooves, and which define a third chord therebetween perpendicular to said reference line, each of said third grooves extending along said upper engaging edge portion.

* * * * *